United States Patent [19]

Giannini et al.

[11] Patent Number: 4,966,770
[45] Date of Patent: Oct. 30, 1990

[54] PREDNISONE MICROENCAPSULATED GRANULES

[75] Inventors: Robert P. Giannini; Stephen Goodstein, both of Plantation, Fla.

[73] Assignee: Himedics, Inc., Hollywood, Fla.

[21] Appl. No.: 385,194

[22] Filed: Jul. 26, 1989

[51] Int. Cl.$^5$ .......... A61K 9/58; A61K 9/62; A61K 9/26; A61K 9/16
[52] U.S. Cl. .................. 424/461; 424/400; 424/439; 424/462; 424/470; 424/493; 424/494; 424/495; 424/497; 424/498
[58] Field of Search .......... 427/3; 424/494, 497, 424/493, 495, 498, 461, 462, 439, 470, 400; 514/974, 885, 886, 922

[56] References Cited

U.S. PATENT DOCUMENTS

| | | | |
|---|---|---|---|
| 4,083,949 | 4/1978 | Benedict | 424/19 |
| 4,138,475 | 2/1979 | McAinsh et al. | 424/19 |
| 4,166,800 | 9/1979 | Hsiao | 427/3 X |
| 4,193,985 | 3/1980 | Bechgaard et al. | 424/19 |
| 4,261,970 | 4/1981 | Ogawa et al. | 424/19 |
| 4,263,273 | 4/1981 | Appelgren et al. | 424/21 |
| 4,341,759 | 7/1982 | Bogentoft et al. | 424/21 |
| 4,508,702 | 4/1985 | Hsiao | 424/19 |
| 4,513,019 | 4/1985 | Brancq et al. | 427/3 |
| 4,587,118 | 5/1986 | Hsiao | 424/19 |
| 4,874,613 | 10/1989 | Hsiao | 424/461 X |

OTHER PUBLICATIONS

Porter, S. C. et al., The Effect of Choice of Process in Drug Release from Non-Pareils Film Coated with Ethyl Cellulose, Proceed. Intern. Symp. Control Rel. Bract. Makr., 12, 41–42, (1985).

Baker, R., Analysis of Oral Dosage Form Patents, 1939 to 1985.

*Primary Examiner*—Thurman K. Page
*Attorney, Agent, or Firm*—Venable, Baetjer, Howard & Civiletti

[57] ABSTRACT

The invention disclosed is prednisone microencapsulated granules with activity densities greater than about 0.030 g/ml. These granules are unusually small, having diameters less than about 1000 microns. The granules are particularly useful in hand-held flowable material dispensers. A process for manufacturing such granules is also disclosed.

42 Claims, No Drawings

PREDNISONE MICROENCAPSULATED GRANULES

BACKGROUND OF THE INVENTION

Over the past several years it has become obvious to health professionals and the pharmaceutical industry that optimal therapy with existing drugs has not been achieved with conventional dosage forms (e.g., tablets, capsules, injectables, suppositories) and dosing regimens. The term "optimal therapy" means the safest, most rapid, and most convenient amelioration of any particular disease state. Further, the "safety" of the dosage form or dosing regimen refers to the frequency and severity of side reactions. Improvement in therapy can then be defined as any change in the dosage form or regimen for an existing drug that:

(1) reduces the frequency and severity of side reactions,
(2) increases the rate at which cure or control is achieved,
(3) decreases the degree of disruption of normal patient activities, and
(4) enhances patient compliance with the prescribed regimen.

In response to this growing perception, a number of novel drug delivery systems have been developed and brought to market. Some good examples are the transdermal delivery devices such as Nitro-Dur ® (Key Pharmaceuticals), Nitro-Disc ®(Searle), Transderm Nitro ® (Ciba), Catapres-TTS ® (Boehringer-Ingelheim) and Transderm-Scop ® (Ciba). Other examples are Theo-Dur ® tablets (Key Pharmaceuticals), a sustained release form of theophylline, Theo-Dur ® Sprinkle (U.S. Pat. No. 4,587,118) and Slo-Bid ™ (Rorer) Theo-Dur ® Sprinkle and Slo-Bid ™ are microencapsulated forms of slow release theophylline that are intended for use in pediatric patients or other patients who may have difficulty in swallowing a tablet. The microcapsules ar supplied in hard gelatin capsules. The hard gelatin capsules are opened at the point of use by the care-giver and administered in a semi-solid food.

This form of drug delivery has significant drawbacks. First, there are a small finite number of capsule sizes marketed, and this limits the physician's ability to prescribe an appropriate dose on the basis of a particular patient's weight, severity of disease, and therapeutic response. Second, there is the possibility of tampering which has become a subject of major concern related to the safety of over-the-counter pharmaceutical products.

Flowable material dispensers such as that described in U.S. Pat. No. 4,579,256 were developed to overcome these drawbacks. The Flowable Material Dispenser is an adjustable, metering and dispensing package. The dispenser can accurately deliver a granular pharmaceutical product to a patient by pouring the selected dosage onto a small quantity of semi-solid food prior to swallowing. The semi-solid food may be contained on a spoon or in a cup. The dispenser is child-resistant, protects the product from the surrounding environment and precisely delivers an adjustable dose well within the compendial requirements for uniformity of dosage units. However, microgranules that are suitable for use in the Flowable Material Dispenser must meet certain narrow specifications with regard to average particle size, particle size distribution, shape, and active agent concentration. These specifications are defined as follows for prednisone microgranules:

Particle size/size distribution (depending on dispenser design):
  Design A: 710 Microns - 1000 Microns
  Design B: 590 Microns - 840 Microns
  Design C: 500 Microns - 710 Microns

| | |
|---|---|
| Activity density (potency × bulk density) | greater than 0.030 g/ml |
| Appearance | nearly spherical |
| Flow | freely flowing |

Although an acceptable product could be made beyond the limits of these parameters, microgranule potency and size must interact to produce a particular activity density which insures that the smallest dose is contained in a volume that is reproducibly measurable while the largest dose is contained in a volume that is convenient to swallow. Small size is also essential if the particles are to be relatively impalpable when added to soft food.

High bulk density is also required if a dispenser of reasonable size for one hand operation is to contain a ten to sixty day supply of drug. Narrow size distribution insures reproducibility of each measured dose and eliminates variation in bulk density due to segregation of sizes. This is critical to a device which measures solid particles by volume. Narrow particle size distribution also implies reproducibility of bulk density from batch to batch. Thus, the same volume will contain the same amount of drug every time in production, which is a new requirement, imposed by the flowable material dispenser but not by conventional delivery systems like hard gelatin capsules. It is also important that the microgranules be nearly spherical to impart the flow characteristics that are required at every stage of assembly and use of the dispenser. The nearly spherical aspect of the microgranules also enhances product elegance.

Presently available conventional pharmaceutically active granules are generally inappropriate for oral administration with semi-solid food or for use in a handheld flowable material dispenser. These conventional granules are large and create a noticeable gritty mouthfeel for the patient. Large microgranule size also necessitates an increase in the smallest characteristic dimension of the measuring cylinder, and the flow channels of the flowable material dispenser if particle bridging is to be avoided. An increase in the smallest characteristic dimension of the measuring cylinder is also necessary if the requirements of the United States Pharmacopeia for Uniformity of Dosage Units are to be met. As those characteristic dimensions increase, so does the overall size of the flowable material dispenser. Each increase in size of the dispenser results in the loss of a degree of convenience in its use. At some microgranule size larger than 18 mesh (1000 microns), the flowable material dispenser becomes too large to be comfortably handheld and hand-operated. Conventional granules are also difficult to accurately dispense from a hand-held flowable material dispenser due to the broad size distribution of granules both within and between batches, as well as the lack of uniform shape of the conventional granules.

Additionally, most pharmaceutically active agents have an unpleasant taste, and many such agents are administered to children who have more taste buds on their tongues than adults and are therefore more cognizant of unpleasant tastes (*Remington's Pharmaceutical Sciences* 15th ed., 1226 (1975)). Some of the pharmaceutically active agents with a more notorious reputation for unpleasant taste include dicloxacillin, erythromycin, cephalosporins and prednisone.

Numerous attempts to mask these unpleasant tastes in conventional dosage forms such as tablets, solutions, and suspensions follow the conventional wisdom of attempting to overpower the unpleasant flavor with a more pleasant one. For example, salty tastes are conventionally masked by syrups such as cinnamon syrup, orange syrup and cherry syrup; bitter tastes are conventionally masked by syrups such as cocoa syrup, raspberry syrup and cherry syrup; acrid or sour tastes are conventionally masked by syrups such as raspberry syrup and acacia syrup; and oily tastes are conventionally masked by syrups such as aromatic rhubarb syrup, compound sarsaparilla syrup and lemon syrup. These conventional taste-masking techniques were more often than not less than satisfactory, particularly in the case of children's medicines.

Prednisone is uniquely suited for incorporation into a flowable material dispenser because a number of important new therapeutic uses are coming to the fore, and the presently available dosage forms are inadequate for the treatment of children in any condition. The presently marketed tablets are too large to be swallowed by children, and the liquids are unpalatable. Similarly, when tablets are crushed to allow easier swallowing the taste is so objectionable that leukemic children have been known to refuse to comply with the prescribed regimen. It is becoming known that hospitalizations due to acute asthma can be significantly reduced by the use of prednisone prophylactically. That is, when an asthmatic child gets a cold, more and more physicians are going to be recommending burst therapy to prevent an attack. At present, 15% of all hospitalizations are due to asthma. Additionally, recent publications suggest that prednisone will be used in combination with antibiotics in otitis media and otitis media with effusion. Given this increasing use of prednisone in seriously ill children, life-threatening treatment failures can be expected unless a more palatable form of the drug is developed. It is this problem that the present invention is intended to eliminate.

SUMMARY OF THE INVENTION

The present invention relates to pharmaceutically active microencapsulated granules comprising prednisone, a binder and a dissolution promoter.

The microencapsulated granules (microgranules) have an unexpectedly rapid rate of dissolution, unique activity density, small size (less than about 1000 microns diameter), narrow size distribution, and uniformity of shape (spherical). A number of binders or combinations of binders may be used in the prednisone granules. Such binders include polyvinylpyrrolidone, hydroxypropyl methylcellulose, polyethylene glycol, hydroxypropyl cellulose and polyethylene oxide. However, a preferred binder is hydroxypropyl methylcellulose, and a preferred dissolution promoter is polyethylene glycol 8000.

The prednisone microgranules also preferably have a taste-mask coating. An acid soluble acrylic resin (Eudragit ® E) is preferred as the taste-mask coating.

The microgranules are preferably manufactured by use of a fluidized bed technique in order to produce microencapsulated granules of uniform small size, uniform concentration of prednisone, narrow range of size distribution and uniform spherical shape. Granules meeting these requirements are intended to be dispensed onto a food product, and therefore the taste-mask coating performs its function by nullifying the unpleasant taste of the pharmaceutically active agent rather than by over powering the unpleasant taste as is attempted with conventional taste-masking techniques. With the granules of the present invention, the patient tastes only the food product because the unpleasant taste of the prednisone has been nullified by the taste-mask coating.

DETAILED DESCRIPTION OF THE INVENTION

The invention relates to prednisone microencapsulated granules with activity densities greater than about 0.030 g/ml. Preferably, the activity density of the microgranules is about 0.050 g/ml to about 0.150 g/ml. Activity density is the product of the microgranule potency multiplied by its bulk density.

Such microgranules are particularly useful in flowable material dispensing devices. One such dispensing device is the "Flowable Material Dispenser" disclosed in U.S. Pat. No. 4,579,256 incorporated herein by reference.

In order for pharmaceutically active microgranules to be used in the above-described dispenser, such microgranules must fall within a narrow range of activity densities, be of small size, narrow size distribution and uniform shape, preferably spherical. They must also be resilient enough to withstand packaging on high speed filling equipment and shipment throughout the world (i.e. not friable). The selected activity density insures that the smallest dose is contained in a volume that is reproducibly measurable while the larger dose is contained in a volume that is convenient to swallow. The uniformly spherical microgranules insure the accuracy and reproducibility of doses from the dispenser. The small size, along with the narrow size distribution of uniformly spherical microgranules are also desirable so that the microgranules do not create an unpleasant gritty feeling in the patient's mouth when the granules are ingested with the food on which they are dispensed. Small average size is also necessary if the flowable material dispenser is to be kept small enough overall to be hand-operated.

In general, the microgranules comprise an inert seed which has a pharmaceutically active coating applied thereto to make a pharmaceutically active seed. A taste mask coating is then applied to the pharmaceutically active seed in a preferred embodiment.

Pharmaceutically active seeds comprise inert seeds to which a pharmaceutically active coating has been applied. Commonly used inert starting seeds on which an active coating composition is applied include nonpareil seeds, sucrose crystals, silica gel and ion exchange resins. The preferred size range for inert starting seeds is inversely related to the average daily dose of the drug in question. In the case of low dose drugs such as prednisone, it is desirable to start with the largest seed possible to obtain the optimal finished drug content. The larger seed size serves to reduce the time required to apply drug to the seeds to meet the finished product seed size requirements of diameters less than 1000 microns. A preferred size is between about 18 mesh and about 25 mesh (about 710 microns to about 1000 microns diameter). The preferred starting seeds for the prednisone microgranules are 25/30 mesh nonpareil seeds.

The pharmaceutically active coating applied to the inert starting seed comprises a mixture of prednisone, a dissolution rate promoting substance (dissolution promoter), and a binder. The ratio of prednisone to binder is in the range of about 10:1 to about 30:1. The ratio of prednisone to dissolution promoting substance is in the range of about 0.3:1 to about 3:1. The mixture preferably comprises about 40% by weight to about 60% by weight prednisone, with about 40% by weight to about 60% by weight dissolution promoter and about 1% by weight to about 5% by weight binder.

Prednisone is a well-known synthetic glucocorticoid having the following formula:

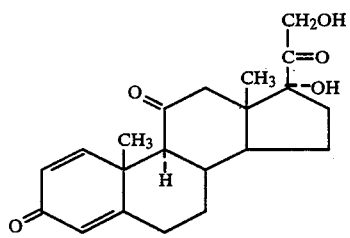

Prednisone occurs as a white, crystalline powder which is very slightly soluble in water and slightly soluble in alcohol. Due to its very slight solubility in water, a micronized form of prednisone is preferred for the present invention.

Prednisone exhibits both antiinflammatory and immunosuppressant effects. Therapeutic dosages of prednisone are based primarily on the condition being treated and the response of the patient. In general, an initial adult dosage of prednisone may range from about 1 to about 60 milligrams daily, usually administered in 2 to 4 divided doses. For children, a prednisone dosage is usually based on body weight (about 0.14–2 mg/kg daily) or body surface area (about 4–60 mg/m$^2$ daily), and administered in 4 divided doses. Once in the human body, prednisone is rapidly reduced in the liver to its 11-hydroxy analog, prednisolone.

Suitable binders for use in the pharmaceutically active coating are conventional binders such as hydroxypropyl methylcellulose, polyvinylpyrrolidone, polyethylene oxide, hydroxypropyl cellulose, and mixtures thereof. A preferred binder is hydroxypropyl methycellulose A dissolution promoter is included in the prednisone microgranule formulation in order to assure that the final product exhibits dissolution characteristics which are equivalent to the dissolution characteristics of convention prednisone preparations, such as Deltasone ® tablets (Upjohn). In the case of a very slightly water soluble active agent such as prednisone, a dissolution promoter may exert its effects simply by means of intimate physical contact with the relatively water insoluble agent or by means of an interaction at a molecular level.

The mixture of prednisone, dissolution promoter and binder is applied to inert seeds as a slurry in a solvent. After the slurry is sprayed onto the seeds, the solvent evaporates, and the water soluble dissolution promoter may physically surround the very slightly water soluble prednisone. This is most probably a physical rather than a molecular level interaction between the prednisone and the dissolution promoter.

The dissolution promoter is effective when present in the formulation at about 60% by weight or less. Suitable dissolution promoters include polyethylene glycol, sucrose and lactose. A preferred dissolution rate promoter is polyethylene glycol, and particularly preferred is polyethylene glycol with an average molecular weight of about 800 (i.e., polyethylene glycol 8000).

Polyethylene glycol is a polymer resin which has the formula:

Where n is greater than or equal to 4, and generally ranges between 4 and about 210. Polyethylene glycol may be prepared by reacting ethylene glycol with ethylene oxide in the presence of sodium hydroxide (NaOH) at temperatures in the range of 120° C. (248° F.) to 135° C. (275° F.) under a pressure of about 4 atmospheres. Depending on its molecular weight, polyethylene glycol may be a clear viscous liquid or a white waxy solid at room temperatures.

Polyethylene glycol with molecular weights between about 190 and about 900 are viscous liquids, while those with molecular weights of about 1000 to about 9000 are waxy solids. The viscosity of polyethylene glycol is measured at 99° C. (210° F.) and ranges from about 4.3 centistokes to about 900 centistokes. The freezing point of polyethylene glycol ranges from about 4° C. (39° F.) to about 63° C. (145° F.). As the molecular weight of polyethylene glycol increases, its water solubility, vapor pressure, hygroscopicity, and solubility in organic solvents decreases, and its freezing or melting range, specific gravity, flash point and viscosity increases. Polyethylene glycol is readily soluble in aromatic hydrocarbons and only slightly soluble in aliphatic hydrocarbons.

Suitable polyethylene glycols are those with molecular weights between about 1000 and about 9000. A preferred polyethylene glycol is that classified as polyethylene glycol 8000, which is available from Union Carbide under the trademark Carbowax ® and from DOW as PEG 8000. This preferred polyethylene glycol has an average molecular weight of about 8000, a viscosity between 470 and 900 centistokes, and a melting range between about 60° C. (140° F.) and 63° C. (145° F.).

The active coating is applied to the inert starting seed as an active coating composition comprising the prednisone/binder/dissolution promoter mixture dispersed in a solvent. Suitable solvents include acetone, water, ethanol, methanol, isopropanol, chloroform, methylene chloride, methyl ethyl ketone, ethyl acetate, carbon tetrachloride, benzene and combinations thereof. Any number of these solvents may be combined to achieve the proper balance between solubility of the binder and dissolution promoter and dispersion of the prednisone while still maintaining a pumpable and sprayable viscosity. Such a desired viscosity is between about 5 centipoise (cps) and about 100 cps as measured by Brookfield viscometer or suitable equivalent instrumentation. A preferred solvent is water.

A taste-mask coating may also be applied to the active seed. Such a taste-mask coating preferably comprises a cationic copolymer of dimethylaminoethyl methacrylate and neutral methacrylic acid esters available from Rohm Tech as Eudragit ® E. The mean molecular weight of Eudragit ® E is 150,000, and it becomes water soluble by forming salts with acids. Film coatings produced from Eudragit ® E are soluble in gastric juice. The Eudragit ® E, which comprises the taste-mask coating is preferably applied to the active seeds as a composition comprising a mixture in a solvent. Suitable solvents for the mixture include methyl alcohol, ethyl alcohol, a (60/40) mixture of ethyl alcohol and water, isopropyl alcohol, n - Butyl alcohol, propylene glycol, ethylene glycol, monobutyl ether, acetone, methyl ethyl ketone, cyclohexanone, methylene chloride, chloroform, carbon tetrachloride, trichloro ethylene, tetrachloro ethylene, ethylacetate, n - Butyl acetate, toluene, propylene glycol acetate or any combination thereof in which Eudragit® E is soluble. A preferred solvent is a mixture of about 40% by weight to about 60% by weight acetone and about 40% by weight to about 60% by weight isopropyl alcohol. When dispensed in the solvent, the Eudragit® E is preferably present as about 12% by weight of the solution.

An alternative taste-mask coating for the prednisone microganules comprises an aqueous dispersion of ethylcellulose (Aquacoat® from FMC) plasticized with acetylated monoglycerides (Myvacet 9-40® from Eastman). This taste-mask coating is present at about 7% by weight to about 23% by weight, and preferably about 15% by weight of the microgranule. The ethycellulose comprises about 85% by weight to about 95% by weight, and preferably about 90% by weight of the taste-mask coating. The remainder of the coating (preferably about 10% by weight) is acetylated monoglycerides.

The ethycellulose/acetylated monoglycerides taste-mask coating is also applied to the active seed as a taste-mask coating composition. This composition preferably comprises an aqueous slurry with a total solids content of about 30% by weight.

The potency of the finished prednisone microencapsulated microgranule is about 50 mg/g to about 250 mg/g. This potency range permits the delivery of a reasonable number of microgranules per desired therapeutic dosage. A therapeutic dose of prednisone microencapsulated microgranules is preferably dispensed onto a patient's food, and should be of a small enough quantity so that the dose is a minor percentage of the quantity of food.

The finished prednisone microencapsulated granules comprise from about 5% to about 25% by weight prednisone, from about 5% to about 25% by weight dissolution promoter, from about 0.25% to about 1.5% by weight binder and from about 7% to about 15% by weight of taste-mask coating. Preferred prednisone microencapsulated granules comprise about 15% by weight prednisone, about 15% by weight polyethylene glycol 8000 as dissolution promoter, about 0.78% by weight hydroxypropyl methylcellulose as binder and about 10% by weight Eudragit® E as the taste-mask coating.

An additional requirement of the finished microgranules is that they be of a uniformly small size, less than about 1000 microns diameter. The finished microgranules preferably have sizes from about 18 mesh (1000 microns diameter) to about 25 mesh (710 microns diameter). The uniformly small size is undetectable by mouthfeel when the patient consumes the food on which the microgranules are dispensed. Larger microgranules tend to create a noticeable gritty mouthfeel when consumed with food.

The uniformly small size of the finished microgranules is also necessary for use of the microgranules in a reasonably sized hand-held dispenser Such hand-held dispensers are the preferred method of dispensing therapeutic doses of prednisone microencapsulated microgranules. Finished microgranules dispensed from a hand-held dispenser are also preferably of a uniformly spherical shape and have a narrow size distribution to insure uniformity of dose.

The preferred characteristics of uniform small size, uniform spherical shape, narrow size distribution and uniform concentration of prednisone are achievable by using a rotor granulator in the manufacture of the prednisone microencapsulated microgranules. Conventional fluidized beds such as Wurster columns or fluid bed granulator/dryers may also be used to manufacture the prednisone microencapsulated microgranules.

In general, a rotor granulator comprises a processing chamber with a rotor at its lower portion. Air is introduced at the level of the rotor for fluidization of the product bed in two ways. Air may enter the chamber through the opening between the rotor and the stator and through a second opening about midway across the radius of the rotor. This introduction of air results in a spiral and twisting air pattern within the chamber. When the inert seeds are introduced into the chamber and coated, the combination of the spinning rotor and the air circulation pattern is purported to provide seeds which have higher individual densities and are rounder and smoother than those produced in conventional fluidized bed systems such as Wurster columns and Glatt fluidized bed granulator/dryers.

Once the starting seeds have been fluidized in the rotor granulator, the active coating composition comprising a suspension of binder, dissolution promoter, and prednisone, is introduced through spray guns mounted in the periphery of the stator near the bottom of the product chamber or near the top of the product chamber to spray on the product from above. Although the starting seeds could also be coated using conventional fluidized beds, the rotor granulator is purported to produce a more evenly coated product with a more uniform, spherical shape.

When used to manufacture prednisone microencapsulated microgranules with a taste-mask coating, inert starting seeds are first fluidized in the processor. The active coating composition is then applied to the inert starting seeds by spray nozzles, to produce pharmaceutically active seeds. When the active seeds have acquired the desired potency, they are dried at about 65° C. (149° F.) in the rotor granulator until a stable product temperature is obtained. The taste-mask coating composition is then applied to the active seeds which are fluidized in the processor. The taste-mask coating composition is applied by spraying through the same nozzles used to spray the pharmaceutically active coating composition. After the desired amount of taste mask coating has been applied, the finished prednisone microencapsulated microgranules are dried in the processor at about 40° C. (105° F.) until a stable product temperature is obtained. These finished microgranules will have the preferred uniform small size (less than about 1000 microns diameter), the uniform spherical shape, narrow size distribution and the preferred concentrations (activity density greater than about 0.030 g/ml).

Despite the purported benefits of the rotor granulator, it has been found that conventional fluidized bed techniques produce prednisone microencapsulated granules which meet all of the requirements for use in a hand-held flowable material dispenser. Such fluidized bed techniques are well known to those skilled in the pharmaceutical manufacturing art. With regard to the present invention, fluidized bed techniques are the preferred method of manufacture for prednisone microencapsulated microgranules.

An additional optional step after the microencapsulated microgranules have been dried is the addition of a sufficient amount of an antistatic agent to uniformly cover the surface of the microgranules. About 0.25% to about 1.5% by weight, and preferably about 0.75% by weight, of the final product weight, of a suitable antistatic agent may be added during the drying step. The fluidized bed is run for about two to about five minutes to distribute the antistatic agent onto the microencapsulated microgranules. This amount of antistatic agent is sufficient to coat the microgranules and to prevent them from sticking to the sides of the flowable material dispenser. The prevention of adherence between the microgranules and the dispenser serves to reduce variability in dosing which is more common when an antistatic agent is not used.

Suitable antistatic agents include silicon dioxide, polacrilin, talc, magnesium stearate, calcium stearate, stearic acid and combinations thereof. The preferred antistatic agent is silicon dioxide. Silicon dioxide, unlike many of the other suitable antistatic agents, serves the dual purpose of also being a moisture scavenger. The elimination of the excess moisture which usually develops from condensation due to climatic changes during shipping and storing, also aids in eliminating variable dosing problems and flow problems with the microgranules.

The finished prednisone microgranules may be used in a variety of dosage delivery systems, including tablets, capsules, unit dose packets, sachets, blisters, and flowable material dispensers. When used in a tablet delivery system, the prednisone microgranules are compressed or formed into a tablet using conventional pharmaceutical tabletting techniques. When used in a capsule delivery system, the prednisone microgranules are used to fill water soluble capsules using conventional pharmaceutical capsule manufacturing techniques. When used in unit dose packets, sachets, or blisters, the prednisone microgranules are used to fill the unit dose packets, sachets or blisters. When used in a flowable material dispenser delivery system, the prednisone microgranules are used to fill the flowable material dispenser.

The features and advantages of the invention are further demonstrated by the following examples. In this specification and in the following examples, all parts and percentages are expressed by weight on an as-is basis, and all temperatures are expressed in degrees Centigrade unless expressly stated to be otherwise.

EXAMPLE 1

Preparation of Prednisone Microencapsulated Granules (871111C)

An active coating composition was formed from 46.95 kg of distilled water, 15.25 kg of polyethylene glycol 8000, 15.28 kg of micronized prednisone, and 0.780 kg of hydroxypropyl methylcellulose E 15 LV. The polyethylene glycol, prednisone and hydroxypropyl methylcellulose were added to the water in a suitable stainless steel tank with vigorous mixing. After the ingredients were dispersed, the mixing speed was reduced and mixing continued for at least 20 minutes.

The active coating composition was applied (sprayed) onto 28.0 kg of 25/30 mesh sugar spheres (starting seeds) to form active seeds. The application of the coating composition took place after the sugar spheres were fluidized in an 18" Wurster column. After all of the active coating composition had been applied, the active seeds were discharged into a suitable container and labelled Prednisone Active Seeds.

A taste-mask coating composition was then prepared by placing 44.0 kg of isopropyl alcohol and 44.0 kg of acetone into a suitable stainless steel tank and mixing in 12.00 kg of Eudragit ® E 100. When complete solution was achieved, the total weight of the mixture was brought to 100.0 kg with additional acetone.

A portion of the taste-mask coating composition (39.4 kg) was applied to a portion (42.53 kg) of the active seeds which were fluidized in the Wurster column.

Finally, 355 g of Silicon Dioxide NF were added to the fluidized, taste-masked microgranules in the column. The column was run for about one minute, after which time the microgranules were coated with the silicon dioxide. These seeds were then discharged into a suitable container and labelled Prednisone Taste-Masked Seeds. Table 1 below shows the amounts of each ingredient in the final product.

TABLE 1

Final Formula
The following table shows the amount of each ingredient per kg of final microgranules and per 30 mg dose of prednisone.

| Quantities (mg) per 30 mg Dose of Prednisone | Ingredients | Quantities (g) per kg of Final Microgranules |
|---|---|---|
| 30.0 | Prednisone, USP | 153.1 |
| 1.5 | Hydroxypropyl Methylcellulose 2910, USP | 7.8 |
| 113.6 | Sugar Spheres, NF | 579.5 |
| 29.9 | Polyethylene Glyol 8000, NF | 152.8 |
| 19.5 | Eudragit ® E-100 | 99.3 |
| 1.51 | Silicon Dioxide, NF | 7.5 |
| 73.2** | Acetone, NF | 363.9** |
| 92.2** | Purified Water, USP | 458.2** |
| 73.2** | Isopropyl Alcohol, NF | 363.9** |

**Removed during processing.

EXAMPLE 2

Effect of the Incorporation of Polyethylene Glycol 8000 on the Dissolution Rate of the Active Seeds An active coating composition was formed from 980 g of distilled water, 495 g of prednisone, and 25 g of hydroxypropyl methylcellulose E 15 LV. This active coating composition was used to create 1,816 g of active seeds in two separate Wurster column runs (870810-A1 and A2) using 800 g and 750 g respectively of 25/30 mesh nonpareils as the starting seeds. The results of dissolution testing on these active seeds are given in Table 2, below.

A second active coating composition was formed from 1,522 g of distilled water, 495 g of prednisone, 25 g of hydroxypropyl methylcellulose, and 495 g of Carbowax ™ 8000. This active coating composition was used to create 2,099 g of active seeds in two separate Wurster column runs (870820-A1 and 870821-A1) using 750 g and 650 g, respectively, of 25/30 mesh non-pareils as the starting seeds. The results of dissolution testing on these active seeds are also given in Table 2, below.

The data in Table 2 show that the addition of polyethylene glycol to the formula in a 1:1 ratio with prednisone clearly reduces the time required to achieve complete dissolution, to the point where it is equivalent to Deltasone ® tablets (Upjohn).

TABLE 2

Effect of the Incorporation of Polyethylene Glycol 8000 on the Dissolution Rate of the Active Seeds
Percent Released

| Lot Number | Time (Minutes) | | | Comments |
|---|---|---|---|---|
| | 10 | 15 | 60 | |
| 870810 A-1 | — | 68 | 90 | Without PEG |
| 870820 A-1 | 97 | — | 103 | With PEG |
| Deltasone ® (098RT) | 100 | — | 100 | |

EXAMPLE 3

Effect of Eudragit ® E-100 Coat Weight on Dissolution and Taste-maskinq Properties Active seeds prepared in accordance with the process described in Example 2 above, (870820-A1 and A2, 870903-A1 and A2, 870915-A1, 870916-A2) containing as much polyethylene glycol 800 as prednisone, were coated with Eudragit ® E-100 (870821-A2, 870904-A1 and A2, 870916-A3 and A4) up to a 20% coating level by weight. Samples were taken at 2, 4, 5, 6, 8, 10, and 15% coat weight. The Eudragit ® E-100 was dissolved at the level of 12% by weight in a mixture of equal parts of aceton and isopropyl alcohol. The samples of product were completely taste-masked at the 5% coating level. All samples released close to 100% of their drug content after 10 minutes in simulated gastric fluid (SGF). (See Table 3 below).

These experiments show that the preferred taste-mask coating level is 10% by weight. This level is sufficiently above the minimum taste-masking requirement and below the maximum level tested so that minor variations in manufacturing parameters will not threaten the taste-masking properties or dissolution profile.

TABLE 3

Effect of Eudragit ® E-100 Coat Weight on Dissolution and Taste-masked Properties
Percent Released

| Lot Number (Coat weight) | Time (Minutes) | | | | | | | | Taste |
|---|---|---|---|---|---|---|---|---|---|
| | 10 | 15 | 20 | 30 | 40 | 45 | 50 | 60 | |
| 870821-A2 (2%) | 96 | — | 99 | 99 | — | 99 | — | 98 | Slightly Bitter |
| 870821-A2 (4%) | — | — | — | — | — | — | — | — | Slightly Bitter |
| 870821-A2 (6%) | — | — | — | — | — | — | — | — | No Taste |
| 870821-A2 (8%) | — | — | — | — | — | — | — | — | No Taste |
| 870821-A2 (10%) | 100 | — | 100 | 100 | — | 101 | — | 100 | No Taste |
| 870904-A1 (5%) | 105 | — | 106 | 106 | — | 105 | — | — | No Taste |
| 870904-A1 (10%) | 104 | — | 107 | 109 | — | 108 | — | — | No Taste |
| 870904-A2 (5%) | 100 | — | 103 | 105 | — | 105 | — | — | No Taste |
| 870904-A2 (10%) | 95 | — | 98 | 99 | — | 99 | — | — | No Taste |
| 870904-A2 (15%) | 101 | — | 103 | 103 | — | 103 | — | — | No Taste |
| 870904-A2 | 103 | — | 106 | 106 | — | 108 | — | — | No |

TABLE 3-continued

Effect of Eudragit ® E-100 Coat Weight on Dissolution and Taste-masked Properties
Percent Released

| Lot Number (Coat weight | Time (Minutes) | | | | | | | | Taste |
|---|---|---|---|---|---|---|---|---|---|
| | 10 | 15 | 20 | 30 | 40 | 45 | 50 | 60 | |
| (20%) | | | | | | | | | Taste |

EXAMPLE 4

Taste-masked Prednisone Microgranules Prepared with Aquacoat ®

Active seeds prepared as described in Example 2, above (870820-A1 and 870821-A1) containing as much polyethylene glycol 800 as prednisone, were coated with Aquacoat ® and plasticized with Myvacet ® 9-40 (870821-A3). The total solids level in the aqueous slurry was 30% by weight. Myvacet was present at a level of 10% of the total solids weight: a total coat weight of 15% was applied with samples taken at 7% and 10%. Dissolution results were encouraging. At the 15% coat level, about 100% of the drug was released in 30 minutes, while about 50% was released in 10 minutes. The product was not perfectly well taste masked at that level but only a slight bitter taste was detected. It is believed that with slight modifications of the Aquacoat ® solids/plasticizer ratio and adjustment of processing parameters, this system could be improved sufficiently to yield an acceptable product.

EXAMPLE 5

Pharmacokinetic Data

Prednisone microencapsulated microgranules which were prepared in accordance with Example 1, above, were compared to a commercially available prednisone tablet formulation (Deltasone ®-Upjohn) to determine relative bioavailability.

Twelve subjects were administered a single dose (30 mg) of each formulation in a randomized, crossover format with each dose separated by at least a 7-day washout period. The subjects were healthy male volunteers, 21 to 39 years of age, and weighed within 10% of ideal body weight. The subjects were determined healthy by physical examination, medical history, and laboratory tests.

The subjects were administered the prednisone formulation with one teaspoonful of applesauce and 180 mL of water.

Fifty (50) milliliters of blood were collected just prior to prednisone administration. After prednisone, seven (7.0) milliliters of blood were collected at each of the following times: 0.25, 0.5,, 1.0, 2, 3, 4, 6, 8, 12, and 24 hours. Each sample of blood was centrifuged as soon as possible after collection. The plasma was separated, quick frozen and stored in the frozen state until just prior to assay. The blood samples were assayed for prednisone and prednisolone using a validated HPLC procedure (for method see: Research Communications in Chemical Pathology and Pharmacology, Vol. 28 No. 1, April, 1980). Prednisone is rapidly reduced to its 11-hydroxy analog, prednisolone, primarily in the liver.

Tables 4 through 14, below, illustrate various pharmacokinetic data of the prednisone microgranules as compared to conventional prednisone tablets (Deltasone ® tablets-Upjohn). Tables 4 and 5, list individual subject and average prednisone plasma concentrations following treatment A (prednisone microgranule formulation) and treatment B (Upjohn's Deltasone ® tablets), respectively. Tables 6 and 7, list individual subject and average prednisolone plasma concentrations following treatments A and B, respectively.

Table 8 lists individual subject and average area under the plasma concentration-time curves ($AUC_{0-12\ hr.}$) for both prednisone and prednisolone following treatments A and B.

Table 9 lists individual subject and average peak plasma concentrations of both prednisone and prednisolone following treatments A and B.

Table 10 lists individual subject and average time to peak plasma concentrations following treatments A and B.

Table 11 lists individual subject and average bioavailabilities-namely $(AUC_{0-12})_A/(AUC_{0-12\ hr.})_B$ and Peak after A/Peak after B with Student t-test showing that the mean ratios do not differ significantly from unity. This is one measure of bioequivalence.

Table 12 lists results of analyses of variance (ANOVA) of $AUC_{0-12\ hr.}$ for prednisone, $AUC_{0-12\ hr.}$ for prednisolone, peak plasma concentration of prednisone, and peak plasma concentration of prednisolone. The treatment mean squares are not significant in each of the four ANOVAs.

Table 13 shows the power ($1-\beta$) of each of the ANOVAs in Table 12. Results in Tables 12 and 13 constitute the former FDA requirement for bioequivalence.

Table 14 shows results of the new FDA requirement for bioequivalence. Since in each case $t_1$ and $t_2$ are both greater than the tabulated t the results support bioequivalence of the prednisone microgranule formulation with Upjohn's Deltasone ® tablets as a reference formulation.

Three different tests were employed to evaluate bioequivalence. These tests are shown in Tables 11-14. It was concluded that prednisone microgranule formulation is bioequivalent relative to Upjohn's Deltasone ® tablets at the 30 mg prednisone level.

TABLE 4

Plasma Concentrations of Prednisone (ng/ml)
Following Treatment A (prednisone microgranule formulation)

| Subject | 0 | 0.25 | 0.5 | 1 | 2 | 3 | 4 | 6 | 8 | 12 | 24 |
|---|---|---|---|---|---|---|---|---|---|---|---|
| 1 | 0 | 23.6 | 33.8 | 39.0 | 51.0 | 49.5 | 28.3 | 20.6 | 16.4 | nd | nd |
| 2 | 0 | 1.5* | 25.4 | 32.6 | 35.8 | 28.9 | 36.7 | 5.5* | 11.9* | nd | nd |
| 3 | 0 | 6.3* | 20.1 | 26.9 | 47.0 | 48.8 | 52.1 | 35.8 | 32.7 | 3.4* | nd |
| 4 | 0 | 9.8* | 21.3 | 25.3 | 38.4 | 27.5 | 26.9 | 13.7 | 9.9* | nd | nd |
| 5 | 0 | nd | 10.4 | 39.3 | 44.4 | 46.8 | 45.5 | 24.8 | 26.9 | 1.1* | nd |
| 6 | 0 | 4.9* | 27.0 | 39.6 | 39.5 | 39.8 | 39.9 | 26.8 | 35.9 | 4.9* | nd |
| 7 | 0 | 4.8* | 76.2 | 20.9 | 46.2 | 31.0 | 39.2 | 31.0 | 22.1 | 6.8* | 4.8* |
| 8 | 0 | 11.3 | 26.9 | 33.0 | 33.7 | 30.7 | 34.1 | 26.5 | 24.0 | 7.8* | nd |
| 9 | 0 | 2.2* | 25.9 | 33.5 | 36.9 | 50.6 | 46.4 | 20.1 | 22.0 | 8.8* | nd |
| 10 | 0 | 20.6 | 31.3 | 33.8 | 40.2 | 38.7 | 36.9 | 25.8 | 17.2 | 8.6* | nd |
| 11 | 0 | 12.7 | 21.4 | 35.9 | 37.2 | 37.8 | 37.9 | 21.8 | 11.7 | 1.8* | nd |
| 12 | 0 | 4.4* | 18.6 | 30.4 | 32.6 | 32.1 | 28.2 | 24.7 | 21.8 | 8.4* | nd |
| MEAN | 0 | 8.51 | 28.2 | 32.5 | 40.2 | 38.5 | 37.7 | 23.1 | 21.0 | 4.3 | |
| S.D. | | 7.45 | 16.3 | 5.84 | 5.72 | 8.61 | 7.75 | 7.84 | 8.17 | 3.66 | |
| C.V.(%) | | 87.6 | 57.9 | 18.0 | 14.2 | 22.4 | 20.6 | 34.0 | 38.9 | 85.1 | |

*Extrapolated value from the standard curve (used in calculating areas under the curves).
nd Not detectable (counted as zero in calculating areas under the curves).

TABLE 5

Plasma Concentrations of Prednisone (ng/ml)
Following Treatment B (Deltasone ®, Upjohn)

| Subject | 0 | 0.25 | 0.5 | 1 | 2 | 3 | 4 | 6 | 8 | 12 | 24 |
|---|---|---|---|---|---|---|---|---|---|---|---|
| 1 | 0 | 6.6* | 16.6 | 23.2 | 30.3 | 33.8 | 37.3 | 14.9 | 13.8 | 5.6* | 1.4* |
| 2 | 0 | 5.8* | 30.9 | 31.7 | 53.8 | 50.2 | 39.2 | 12.3 | 14.2 | nd | nd |
| 3 | 0 | 3.8* | 9.0* | 29.7 | 52.4 | 47.9 | 48.5 | 31.2 | 29.0 | 8.7* | 2.2* |
| 4 | 0 | 13.3 | 22.9 | 24.7 | 32.2 | 27.7 | 23.6 | 14.7 | 9.5* | nd | nd |
| 5 | 0 | nd | 16.3 | 42.1 | 54.7 | 47.3 | 44.6 | 20.8 | 21.8 | nd | nd |
| 6 | 0 | 3.0* | 22.4 | 32.6 | 33.7 | 37.2 | 39.4 | 261.0 | 21.3 | 2.4* | nd |
| 7 | 0 | nd | 13.5 | 30.1 | 38.4 | 43.7 | 39.2 | 31.8 | 23.7 | 12.3 | nd |
| 8 | 0 | nd | nd | 19.8 | 56.8 | 41.9 | 37.3 | 21.9 | 23.0 | 9.4* | nd |
| 9 | 0 | 4.6* | 18.9 | 27.8 | 43.5 | 37.6 | 29.5 | 21.6 | 24.9 | 4.7* | nd |
| 10 | 0 | 13.9 | 29.5 | 40.6 | 43.3 | 37.4 | 34.9 | 26.1 | 14.6 | 7.0* | nd |
| 11 | 0 | nd | 8.0* | 34.1 | 39.2 | 39.4 | 35.5 | 16.1 | 9.9* | 2.9* | nd |
| 12 | 0 | 20.2 | 37.0 | 28.9 | 31.8 | 32.6 | 31.3 | 19.5 | 20.1 | 5.8* | nd |
| MEAN | 0 | 5.93 | 18.8 | 30.4 | 42.5 | 39.7 | 36.7 | 21.4 | 18.8 | 4.90 | |
| S.D. | | 6.59 | 10.6 | 6.52 | 9.79 | 6.75 | 6.60 | 6.39 | 6.25 | 4.02 | |
| C.V.(%) | | 111. | 56.2 | 21.4 | 23.0 | 17.0 | 18.0 | 29.9 | 33.2 | 82.0 | |

See the footnotes of the previous Table.

TABLE 6

Plasma Concentrations of Prednisolone (ng/ml) Following Treatment A (prednisone microgranule formulation)

| Subject | 0 | 0.25 | 0.5 | 1 | 2 | 3 | 4 | 6 | 8 | 12 | 24 |
|---|---|---|---|---|---|---|---|---|---|---|---|
| 1 | 0 | 497.0* | 418.0* | 436.3 | 459.9 | 452.6 | 256.0 | 169.1 | 92.5 | 39.1 | nd |
| 2 | 0 | 253.9 | 417.2 | 405.1 | 338.2 | 236.4 | 215.5 | 100.4 | 79.1 | 5.3* | nd |
| 3 | 0 | 218.1 | 304.7 | 347.2 | 389.8 | 349.9 | 281.8 | 209.4 | 129.1 | nd | nd |
| 4 | 0 | 284.9 | 400.5 | 336.5 | 367.8 | 198.7 | 99.6 | 136.7 | 97.0 | 28.8 | nd |
| 5 | 0 | 79.5 | 313.8 | 553.6 | 434.9 | 341.9 | 297.5 | 214.8 | 139.0 | 41.7 | 3.2* |
| 6 | 0 | 240.0 | 598.6 | 540.0 | 388.6 | 358.0 | 303.2 | 188.8 | 89.8 | 42.9 | nd |
| 7 | 0 | 125.6 | 512.2 | 249.6 | 369.7 | 216.2 | 215.6 | 164.2 | 99.7 | 38.1 | nd |
| 8 | 0 | 195.4 | 479.3 | 481.9 | 409.7 | 352.2 | 300.3 | 128.6 | 79.7 | 38.1 | nd |
| 9 | 0 | 152.2 | 542.4 | 420.4 | 303.4 | 328.3 | 283.2 | 145.1 | 110.1 | 41.0 | nd |
| 10 | 0 | 347.8 | 455.3 | 363.2 | 338.4 | 244.3 | 211.5 | 144.4 | 92.2 | 34.7 | nd |
| 11 | 0 | 191.5 | 391.9 | 423.8 | 287.4 | 229.0 | 196.9 | 115.3 | 56.7 | 5.8* | nd |
| 12 | 0 | 103.1 | 423.5 | 480.5 | 338.5 | 278.5 | 240.5 | 162.6 | 114.3 | 28.8 | nd |
| MEAN | 0 | 224.1 | 438.1 | 419.8 | 368.0 | 298.8 | 241.8 | 156.6 | 98.3 | 28.7 | |
| S.D. | | 115.6 | 86.3 | 87.8 | 51.8 | 76.5 | 59.0 | 35.4 | 22.5 | 15.8 | |
| C.V.(%) | | 51.6 | 19.7 | 20.9 | 14.1 | 25.6 | 34.4 | 22.6 | 22.9 | 55.0 | |

See the footnotes of the previous Table.

TABLE 7

Plasma Concentrations of Prednisolone (ng/ml) Following Treatment B (Deltasone ®, Upjohn)

| Subject | 0 | 0.25 | 0.5 | 1 | 2 | 3 | 4 | 6 | 8 | 12 | 24 |
|---|---|---|---|---|---|---|---|---|---|---|---|
| 1 | 0 | 286.6 | 412.9 | 386.4 | 314.6 | 279.0 | 246.6 | 125.4 | 91.9 | 34.0 | nd |
| 2 | 0 | 442.5 | 389.6 | 337.0 | 364.7 | 292.4 | 222.3 | 142.2 | 89.8 | 19.0* | nd |
| 3 | 0 | nd | 191.1 | 381.9 | 381.1 | 319.5 | 283.4 | 174.5 | 132.1 | 43.3 | nd |
| 4 | 0 | 372.8 | 429.3 | 340.0 | 351.6 | 291.9 | 237.6 | 138.9 | 91.8 | 30.4 | nd |
| 5 | 0 | 82.3 | 321.3 | 559.1 | 436.1 | 304.0 | 278.3 | 187.0 | 95.0 | 51.1 | nd |
| 6 | 0 | 196.1 | 484.7 | 447.2 | 342.2 | 349.7 | 297.9 | 172.9 | 117.3 | 26.9 | nd |
| 7 | 0 | 171.2 | 313.7 | 430.3 | 334.9 | 337.2 | 253.6 | 206.9 | 125.0 | 53.6 | nd |
| 8 | 0 | nd | nd | 222.8 | 372.7 | 443.8 | 368.3 | 196.9 | 164.3 | 71.7 | nd |
| 9 | 0 | 224.3 | 414.4 | 349.3 | 352.0 | 304.7 | 227.9 | 168.4 | 132.0 | 43.0 | nd |
| 10 | 0 | 229.6 | 412.8 | 410.5 | 342.2 | 231.9 | 191.1 | 138.3 | 68.1 | 22.5 | nd |
| 11 | 0 | 16.3* | 225.9 | 426.0 | 321.2 | 255.7 | 229.4 | 110.6 | 58.2 | 17.6* | nd |
| 12 | 0 | 477.9 | 434.0 | 430.2 | 351.0 | 279.2 | 216.9 | 125.4 | 87.5 | 18.0* | nd |
| MEAN | | 0 | 208.3 | 335.8 | 393.4 | 355.4 | 307.5 | 254.5 | 157.3 | 104.4 | 35.9 |
| S.D. | | 165.8 | 137.5 | 80.7 | 31.9 | 53.8 | 47.1 | 31.2 | 30.2 | 17.0 | |
| C.V.(%) | | 79.6 | 40.9 | 20.5 | 8.98 | 17.5 | 18.5 | 19.8 | 29.0 | 47.3 | |

See the footnotes of the previous Table.

TABLE 8

Areas Under Plasma Concentration-Time Curves by Trapezoidal Rule $$\text{AUC 0-12 Hr} \left( \frac{ng}{ml} \times hr \right)$$

| | PREDNISONE | | PREDNISOLONE | |
|---|---|---|---|---|
| Subject | Treatment A (prednisone microgranule) | Treatment B (Upjohn Deltasone ® tablet) | Treatment A (prednisone microgranule) | Treatment B (Upjohn Deltasone ® tablet) |
| 1 | 281.1 | 227.7 | 2599 | 2075 |
| 2 | 200.8 | 266.8 | 1870 | 2092 |
| 3 | 379.7 | 366.5 | 2398 | 2316 |
| 4 | 192.8 | 183.6 | 1812 | 2123 |
| 5 | 325.3 | 313.6 | 2706 | 2479 |
| 6 | 351.3 | 284.3 | 2624 | 2456 |
| 7 | 295.4 | 327.8 | 2024 | 2432 |
| 8 | 293.8 | 301.1 | 2375 | 2566 |
| 9 | 316.3 | 281.7 | 2316 | 2291 |
| 10 | 296.9 | 288.0 | 2065 | 1907 |
| 11 | 252.3 | 406.2 | 1737 | 1760 |
| 12 | 269.5 | 262.9 | 2248 | 2110 |
| MEAN | 287.9 | 292.5 | 2231 | 2218 |
| S.D. | 54.9 | 58.8 | 329.2 | 246.8 |
| C.V. (%) | 19.1 | 20.1 | 14.8 | 11.1 |

TABLE 9

| | Peak Plasma Concentration (ng/ml) | | | |
|---|---|---|---|---|
| | PREDNISONE | | PREDNISOLONE | |
| Subject | Treatment A (prednisone microgranule) | Treatment B (Upjohn) Deltasone ® tablet) | Treatment A (prednisone microgranule) | Treatment B (Upjohn) Deltasone ® tablet) |
| 1 | 51.0 | 37.3 | 459.9 | 412.9 |
| 2 | 35.8 | 53.8 | 417.2 | 422.5 |
| 3 | 52.1 | 52.4 | 389.8 | 381.9 |
| 4 | 38.4 | 32.2 | 367.8 | 429.3 |
| 5 | 46.8 | 54.7 | 553.6 | 559.1 |
| 6 | 39.9 | 39.4 | 598.6 | 484.7 |
| 7 | 46.2 | 43.7 | 512.2 | 430.3 |
| 8 | 34.1 | 56.8 | 481.9 | 443.8 |
| 9 | 50.6 | 43.5 | 542.4 | 414.4 |
| 10 | 40.2 | 43.3 | 455.3 | 412.8 |
| 11 | 37.9 | 39.4 | 423.8 | 426.0 |
| 12 | 32.6 | 37.0 | 480.5 | 477.9 |
| MEAN | 42.1 | 44.5 | 473.6 | 443.0 |
| S.D. | 6.90 | 8.08 | 69.3 | 46.2 |
| C.V. (%) | 16.4 | 18.2 | 14.6 | 10.4 |

TABLE 10

| | Time of Peak Plasma Concentrations (Hours) | | | |
|---|---|---|---|---|
| | PREDNISONE | | PREDNISOLONE | |
| Subject | Treatment A (prednisone microgranule) | Treatment B (Upjohn) Deltasone ® tablet) | Treatment A (prednisone microgranule) | Treatment B (Upjohn) Deltasone ® tablet) |
| 1 | 2 | 4 | 2 | 0.5 |
| 2 | 2 | 2 | 0.5 | 0.25 |
| 3 | 4 | 2 | 2 | 1 |
| 4 | 2 | 2 | 2 | 0.5 |
| 5 | 3 | 2 | 1 | 1 |
| 6 | 4 | 4 | 0.5 | 0.5 |
| 7 | 2 | 3 | 0.5 | 1 |
| 8 | 4 | 2 | 1 | 3 |
| 9 | 3 | 2 | 0.5 | 0.5 |
| 10 | 2 | 2 | 0.5 | 0.5 |
| 11 | 4 | 3 | 1 | 1 |
| 12 | 2 | 0.5 | 1 | 0.25 |
| MEAN | 2.8 | 2.4 | 1.0 | 0.83 |
| S.D. | 0.94 | 0.98 | 0.62 | 0.74 |
| C.V. (%) | 33.0 | 41.0 | 62.0 | 89.0 |

| | ANALYSIS OF VARIANCE | | | | |
|---|---|---|---|---|---|
| Source of Variation | d.f. | Sum of Squares | Mean Square | F | p |
| Groups Subjects | 1 | 1.2604 | 1.2604 | 1.14 | p > 0.25 |
| Subj/Group | 10 | 11.1042 | 1.1104 | — | |
| Treatments | 1 | 1.2604 | 1.2604 | 1.62 | 0.25 > p > 0.10 |
| Time periods | 1 | 0.09375 | 0.09375 | 0.121 | p > 0.25 |
| Residual | 10 | 7.77083 | 0.77708 | — | |
| | 23 | 21.48958 | | | |

$$\text{C.V. from RMS} = \frac{\sqrt{0.77708}}{2.60} \times 100 = 33.9\%$$

TABLE 11

| | Individual Subject Bioavailabilities | | | |
|---|---|---|---|---|
| | $\dfrac{(\text{AUC 0-12 Hr})_A}{(\text{AUC 0-12 Hr})_B}$ | | $\dfrac{\text{Peak after A}}{\text{Peak after B}}$ | |
| SUBJECT | PREDNISONE | PREDNISOLONE | PREDNISONE | PREDNISOLONE |
| 1 | 1.23 | 1.25 | 1.37 | 1.11 |
| 2 | 0.753 | 0.894 | 0.665 | 0.943 |
| 3 | 1.04 | 1.04 | 0.994 | 1.02 |
| 4 | 1.05 | 0.850 | 1.19 | 0.857 |
| 5 | 1.04 | 1.09 | 0.856 | 0.990 |
| 6 | 1.24 | 1.07 | 1.01 | 1.23 |
| 7 | 0.901 | 0.832 | 1.06 | 1.19 |
| 8 | 0.976 | 0.926 | 0.600 | 1.09 |
| 9 | 1.12 | 1.01 | 1.16 | 1.31 |
| 10 | 1.03 | 1.08 | 0.928 | 1.10 |
| 11 | 0.6221 | 0.987 | 0.962 | 0.995 |
| 12 | 1.03 | 1.07 | 0.881 | 1.01 |
| MEAN ($\overline{X}$) | 0.984 | 1.01 | 0.948 | 1.07 |
| S.E.M.* | 0.575 | 0.0341 | 0.0644 | 0.0369 |
| $t = \dfrac{1 - \overline{X}}{\text{S.E.M.}}$ | 0.28 | 0.29 | 0.81 | 1.90 |

TABLE 11-continued

| | Individual Subject Bioavailabilities | | | |
|---|---|---|---|---|
| | $\dfrac{(AUC\ 0-12\ Hr)_A}{(AUC\ 0-12\ Hr)_B}$ | | Peak after A / Peak after B | |
| SUBJECT | PREDNISONE | PREDNISOLONE | PREDNISONE | PREDNISOLONE |
| p | p > 0.25 | p > 0.25 | p > 0.25 | 0.10 > p > 0.05 |

*The standard error was calculated by a method which took into account the variance of both numerator and denominator forming the ratio.

Conclusions from the data in Table 11 above

The prednisone microganule formulation was bioequivalent to the reference formulation (Upjohn's Deltasone ® tablets) by this method. The prednisone microgranule formulation passes the 75-75-125 "rule".

TABLE 12

| Analyses of Variance for Crossover Design | | | | | |
|---|---|---|---|---|---|
| Source of Variation | d.f. | Sum of Squares | Mean Squares | F | p |
| ANOVA of AUC 0-12 hr-PREDNISONE | | | | | |
| Groups Subjects | 1 | 14,084.41 | 14,084.41 | 3.70 | NS (0.1 > p > 0.05) |
| Subj/Group | 10 | 38,044.82 | 3,804.48 | — | |
| Treatments | 1 | 123.31 | 123.31 | 0.066 | p > 0.25 |
| Time Periods | 1 | 346.56 | 346.56 | 0.186 | p > 0.25 |
| Residual | 10 | 18,662.61 | 1,866.26 | — | |
| Total | 23 | 71,261.71 | | | |

C.V. (%) from RMS = $\dfrac{\sqrt{1,866.26}}{290.2} \times 100 = 14.9\%$

| ANOVA of AUC 0-12 hr-PREDNISOLONE | | | | | |
|---|---|---|---|---|---|
| Groups Subjects | 1 | 31,901. | 31,901. | 0.22 | p > 0.25 |
| Subj/Group | 10 | 1,448,640. | 144,864. | — | |
| Treatments | 1 | 1,027. | 1,027. | 0.028 | p > 0.25 |
| Time Periods | 1 | 20,242. | 20,242. | 0.56 | p > 0.25 |
| Residual | 10 | 359,474. | 35,947. | — | |
| Total | 23 | 1,861,284. | | | |

C.V. (%) from RMS = $\dfrac{\sqrt{35,947}}{2225} \times 100 = 8.52\%$

| ANOVA of Peak Concentration-PREDNISONE | | | | | |
|---|---|---|---|---|---|
| Groups Subjects | 1 | 216.6 | 216.6 | 4.81 | NS (0.1 > p > 0.25) |
| Subj/Group | 10 | 450.56 | 45.056 | — | |
| Treatments | 1 | 32.43 | 32.43 | 0.72 | p > 0.25 |
| Time Periods | 1 | 126.50 | 126.50 | 2.81 | |
| Residual | 10 | 449.09 | 44.909 | — | |
| Total | 23 | 1,275.18 | | | |

C.V. (%) from RMS = $\dfrac{\sqrt{44.909}}{43.3} \times 100 = 15.5\%$

| ANOVA of Peak Concentration-PREDNISOLONE | | | | | |
|---|---|---|---|---|---|
| Groups Subjects | 1 | 8.17 | 8.17 | 0.0014 | p > 0.25 |
| Subj/Group | 10 | 58,796.72 | 5,879.57 | — | |
| Treatments | 1 | 5,624.29 | 5,624.29 | 3.40 | NS (0.1 > p > 0.05) |
| Time Periods | 1 | 897.93 | 897.93 | 0.54 | p > 0.25 |
| Residual | 10 | 16,506.93 | 1,650.69 | — | |
| | 23 | 81,833.04 | | | |

C.V. (%) from RMS = $\dfrac{\sqrt{1,650.7}}{458.3} \times 100 = 8.87\%$

TABLE 13

| Power of the Analyses of Variance form a 20% Difference in Means | | | | |
|---|---|---|---|---|
| ANOVA | Φ | $v_1$ | $v_2$ | power = 1-β |
| AUC 0-12 hr-PREDNISONE | 2.582 | 1 | 10 | >0.99 |
| AUC 0-12 hr-PREDNISOLONE | 4.533 | 1 | 10 | >0.99 |
| Peak Conc.-PREDNISONE | 2.483 | 1 | 10 | >0.99 |

TABLE 13-continued

| Power of the Analyses of Variance form a 20% Difference in Means | | | | |
|---|---|---|---|---|
| ANOVA | Φ | $v_1$ | $v_2$ | power = 1-β |
| Peak Conc.-PREDNISOLONE | 4.340 | 1 | 10 | >0.99 |

Reference: J. G. Wagner, Fundamentals of Clinical Pharmacokinetics, Drug Intelligence Publications, Hamilton, IL, 1975, pp. 301-303.

Conclusions from Tables 12 and 13.

The treatment mean squares were not significant and there was very high power for parameters studied, namely AUC 0-12 hr for prednisone, AUC 0-12 hr for prednisolone, peak plasma concentration of prednisone and peak plasma concentration of prednisolone.

TABLE 14

Two One Sided Test Procedure for Bioequivalence $$t_1 = (X_T - X_B) - \theta_1$$
$$t_2 = (\theta_2 - (X_T - X_R))$$

| Data | $\theta_1 = -0.2\, X_R$ | $\theta_2 = 0.2\, X_R$ | $s\sqrt{\frac{2}{N}}$ | $s\sqrt{\frac{2}{N}}$ |
|---|---|---|---|---|
| AUC 0–12 hr PREDNISONE | −58.5 | 58.5 | 3.06 | 3.06 |
| AUC 0–12 hr PREDNISOLONE | −443.6 | 443.6 | 5.90 | 5.56 |
| Peak Concn. PREDNISONE | −8.9 | 8.9 | 2.38 | 2.38 |
| Peak Concn. PREDNISOLONE | −88.6 | 88.6 | 7.18 | 3.49 |

Reference: D. J. Schuirmann, J. Pharmacokinet. Biopharm. 15: 657–680, 1987, No. 6.
*The tabled $t_{N-2, 0.95} = 1.8125$.

*Conclusion from Table 14 above

The prednisone microgranule formulation was bioequivalent to the reference formulation (Upjohn's Deltasone® tablets) for all four parameters listed in column 1 of Table 14 above and both $t_1$ and $t_2$ were both greater than the tabulated t.

EXAMPLE 6

Stability of the Prednisone Microgranule

Three batches of prednisone taste-masked microgranules, produced according to Example 1 were entered into a stability program. Two of the batches were made in production scale equipment (45 kg). The other was a laboratory scale batch (0.8 kg). The microgranules were stored in prototype hiMEDICS dispensers as described in U.S. Pat. No. 4,579,256. Further details of the studies and the results are presented in Table 15 through 17 below. After 9 months storage at room temperature, there was no change in any of the measured parameters of the prednisone microgranules. Most importantly, there was no change in potency, dissolution, or taste. Similarly, after 6 months storage at 37° C. and 75% relative humidity there was no change in the measured parameters of the microgranules.

TABLE 15

LOT #: 871111C-1    Storage Conditions
Theoretical Potency (mg/g): 150.0

| Parameter & Method | Initial | 3M RT | 6M RT | 9M RT | Specifications |
|---|---|---|---|---|---|
| Potency (mg/g) M-010 | 152.7 | 151.8 | 152.5 | 151.1 | 135.0–165.0 mg/g |
| Potency (% of Theory) | 101.8 | 101.2 | 101.7 | 101.8 | |
| Potency (% of Initial) | 100.0 | 99.4 | 99.9 | 99.0 | |
| Identification, M-010 | Pass | Pass | Pass | Pass | Meets Test |
| Loss on Drying (% w/w) 3 hrs. 60° C. under vacuum | 0.54 | 0.69 | 0.65 | 0.77 | NMT 3.0% |
| Water (%), USP XXI (921) | 0.92 | 0.42 | 0.99 | 1.24 | NMT 3.0% |
| Appearance, M-002 | Pass | Pass | Pass | Pass | White to off-white Free flowing, uniform spheres |
| Odor, M-006 | None | None | None | None | Report odor |
| Taste, M-008 | Pass | Pass | Pass | Pass | None to slightly bitter |
| Bulk Density (g/ml), M-004 | 0.798 | 0.803 | 0.751 | 0.739 | Report Value |
| Dissolution, % LC Dissolved Fluid: SGF USP Apparatus I @ 100 rpm, M-009 | | | | | |
| Interval - 30 Min. | 102.6 | 103.2 | 101.4 | 105.8 | |

Storage Conditions:
RT = Room Temperature 15–30°C.
37/75 = 35–40° C. with 70–80% relative humidity
NMT = not more than

| Parameter & Method | Initial | 1M 37/75 | 2M 37/75 | 3M 37/75 | 6M 37/75 | Specifications |
|---|---|---|---|---|---|---|
| Potency (mg/g) | 152.7 | 162.8 | 151.9 | 154.3 | 152.7 | 135–165.0 mg/g |
| Potency (% of Theory) | 101.8 | 108.5 | 101.3 | 102.9 | 101.8 | |
| Potency (% of Initial) | 100.0 | 106.6 | 99.5 | 101.0 | 100.0 | |
| Identification, M-010 | Pass | Pass | Pass | Pass | Pass | Meets Test |
| Loss on Drying (% w/w) 3 hrs. 60' C. under vacuum | 0.54 | 1.21 | 1.17 | 1.65 | 1.65 | NMT 3.0% |
| Water (%), USP XXI (921) | 0.92 | 1.63 | 1.38 | 0.84 | 1.55 | NMT 3.0% |
| Appearance, M-022 | Pass | Pass | Pass | Pass | Pass | White to off-white Free flowing, uniform spheres |
| Odor, M-006 | None | None | None | None | None | Report odor |
| Taste, M-008 | Pass | Pass | Pass | Pass | Pass | None to slightly bitter |
| Bulk Density (g/ml), M-004 | 0.798 | 0.778 | 0.802 | 0.720 | Report Value | |
| Dissolution, % LC Dissolved Fluid: SGF USP Apparatus I @ 100 rpm, M-009 | | | | | | |
| Interval - 30 Min. | 102.6 | 94.0 | 94.8 | 100.6 | 100.0 | NLT 80% @ 30 Min. |

Storage Conditions
RT = Room Temperature 15–30° C.
37/75 = 35–40° C. with 70–80% relative humidity
NMT = not more than
NLT = not less than

TABLE 16

| LOT #: 871111B-1 | Storage Conditions Theoretical Potency (mg/g): 150.0 | | | | |
|---|---|---|---|---|---|
| Parameter & Method | Initial | 3M RT | 6M RT | 9M RT | Specifications |
| Potency (mg/g) | 153.1 | 153.8 | 154.7 | 152.6 | 135.0–165.0 mg/g |
| Potency (% of Theory) | 102.1 | 102.5 | 103.1 | 101.7 | |
| Potency (% of Initial) | 100.0 | 100.5 | 101.0 | 99.7 | |
| Identification, M-010 | Pass | Pass | Pass | Pass | Meets Test |
| Loss on Drying (% w/w) 3 hrs. 60° C. under vacuum | 0.65 | 0.99 | 0.55 | 0.79 | NMT 3.0% |
| Water (%), USP XXI (921) | 1.35 | 0.72 | 0.99 | 1.12 | NMT 3.0% |
| Appearance, M-002 | Pass | Pass | Pass | Pass | White to off-white Free flowing, uniform spheres |
| Odor, M-006 | None | None | None | None | Report odor |
| Taste, M-008 | Pass | Pass | Pass | Pass | None to slightly bitter |
| Bulk Density (g/ml), M-004 | 0.775 | 0.790 | 0.758 | 0.737 | Report Value |
| Dissolution, % LC Dissolved Fluid: SGF USP Apparatus I @ 100 rpm, M-009 | | | | | |
| Interval - 30 Min. | 101.8 | 103.4 | 99.4 | 106.0 | |
| Storage Conditions: | RT = Room Temperature 15–30° C. 37/5 = 35–40° C. with 70–80% relative humidity NMT = not more than | | | | |
| Parameter & Method | Initial | 1M 37/75 | 2M 37/75 | 3M 37/75 | 6M 37/75 | Specifications |
| Potency (mg/g) | 153.1 | 159.4 | 146.4 | 151.8 | 152.4 | 135.0–165.0 mg/g |
| Potency (% of Theory) | 102.1 | 106.3 | 97.6 | 101.2 | 101.6 | |
| Potency (% of Initial) | 100.0 | 104.1 | 95.6 | 99.2 | 99.5 | |
| Identification, M-010 | Pass | Pass | Pass | Pass | Pass | Meets Test |
| Loss on Drying (% w/w) 3 hrs. 60° C. under vacuum | 0.65 | 1.20 | 1.25 | 1.01 | 1.66 | NMT 3.0% |
| Water (%), USP XXI (921) | 1.35 | 1.16 | 1.65 | 1.36 | 0.99 | NMT 3.0% |
| Appearance, M-002 | Pass | Pass | Pass | Pass | Pass | White to off-white Free flowing, uniform spheres |
| Odor, M-006 | None | None | None | None | None | Report odor |
| Taste, M-008 | Pass | Pass | Pass | Pass | Pass | None to slightly bitter |
| Bulk Density (g/ml), M-004 | 0.775 | 0.799 | 0.816 | 0.802 | 0.782 | Report Value |
| Dissolution, % LC Dissolved Fluid: SGF USP Apparatus I @ 100 rpm, M-009 | | | | | | |
| Interval - 30 Min. | 101.8 | 94.7 | 95.2 | 101.6 | 99.0 | NLT 80% @ 30 Min. |
| Storage Conditions: | RT = Room Temperature 15–30° C. 37/35 = 35–40° C. with 70–80% relative humidity NMT = not more than | | | | | |

TABLE 17

| LOT #: 871111A-1 | Storage Conditions Theoretical Potency (mg/g): 153.0 | | | | |
|---|---|---|---|---|---|
| Parameter & Method | Initial | 3M RT | 6M RT | 9M RT | Specifications |
| Potency (mg/g) | 155.0 | 153.8 | 154.9 | 157.0 | 135.0–165.0 mg/g |
| Potency (% of Theory) | 101.3 | 100.5 | 101.2 | 102.6 | |
| Potency (% Initial) | 100.0 | 99.2 | 99.9 | 101.3 | |
| Identification, M-010 | Pass | Pass | Pass | Pass | Meets Test |
| Loss on Drying (% w/w) 3 hrs. 60' under vacuum | 0.61 | 0.84 | 0.56 | 0.64 | NMT 3.0% |
| Water (%), USP XXI (921) | 1.30 | 0.55 | 0.85 | 0.95 | NMT 3.0% |
| Appearance, M-002 | Pass | Pass | Pass | Pass | White to off-white Free flowing, uniform spheres |
| Odor, M-006 | None | None | None | None | Report odor |
| Taste, M-008 | Pass | Pass | Pass | Pass | None to slightly bitter |
| Bulk Density (g/ml), M-004 | 0.802 | 0.787 | 0.764 | 0.729 | Report Value |
| Dissolution, % LC Dissolved Fluid: SGF USP Apparatus I @ 100 rpm, M-009 | | | | | |
| Interval - 30 Min. | 107.3 | 105.4 | 97.2 | 93.8 | |
| Storage Conditions: | RT = Room Temperature 15–30° C. 37/75 = 35–40° C. with 70–80% relative humidity NMT = not more than | | | | |
| Parameter & Method | Initial | 1M 37/75 | 2M 37/75 | 3M 37/75 | 6M 37/75 | Specifications |
| Potency (mg/g) | 155.0 | 161.2 | 144.3 | 155.9 | 152.9 | 135.0–165.0 mg/g |
| Potency (% of Theory) | 101.3 | 105.4 | 94.3 | 101.9 | 99.9 | |
| Potency (% of Initial) | 100.0 | 104.0 | 93.1 | 100.6 | 98.6 | |
| Identification, M-010 | Pass | Pass | Pass | Pass | Pass | Meets Test |
| Loss on Drying (% w/w) | 0.61 | 1.23 | 0.88 | 1.67 | 1.41 | NMT 3.0% |

TABLE 17-continued

| LOT #: 871111A-1 | Storage Conditions | | | | | |
|---|---|---|---|---|---|---|
| | Theoretical Potency (mg/g): 153.0 | | | | | |
| 3 hrs. 60° C. under vacuum | | | | | | |
| Water (%), USP XXI (921) | 1.30 | 0.80 | 1.74 | 1.05 | 1.97 | NMT 3.0% |
| Appearance, M-002 | Pass | Pass | Pass | Pass | Pass | White to off-white Free flowing, uniform spheres |
| Odor, M-006 | None | None | None | None | None | Report odor |
| Taste, M-008 | Pass | Pass | Pass | Pass | Pass | None to slightly bitter |
| Bulk Density (g/ml), M-004 | 0.802 | 0.768 | 0.790 | 0.790 | 0.723 | Report Value |
| Dissolution, % LC Dissolved Fluid: SGF USP Apparatus I @ 100 rpm, M-009 | | | | | | |
| Interval - 30 Min. | 107.3 | 105.0 | 90.9 | 102.5 | 99.5 | NLT 80% @ 30 Min. |
| Storage Conditions: | RT = Room Temperature 15–30° C. | | | | | |
| | 37/75 = 35–40° C. with 70–80% relative humidity | | | | | |
| | NMT = not more than | | | | | |
| | NLT = not less than | | | | | |

While the invention has been disclosed by reference to the details of various embodiments of the invention, it is understood that this disclosure is intended in an illustrative rather than in a limiting sense, as it is contemplated that modification will occur to those skilled in the art, within the spirit of the invention and the scope of the appended claims.

What is claimed is:

1. A microencapsulated granule comprising a mixture of about 5% by weight to about 25% by weight prednisone, about 5% to about 25% by weight of a dissolution promoter and about 0.25% to about 1.5% by weight of a binder as an active coating on an inert seed, said granule having an activity density greater than about 0.030 g/ml and a diameter less than about 1000 microns.

2. The microencapsulated granule of claim 1 wherein the binder is selected from the group consisting of hydroxypropyl methylcellulose, polyvinylpyrrolidone, polyethylene oxide, hydroxypropyl cellulose and combinations thereof, and said dissolution promoter is selected from the group consisting of polyethylene glycol, sucrose, lactose and combinations thereof.

3. The microencapsulated granule of claim 2 wherein said binder is hydroxypropyl methycellulose and said dissolution promoter is polyethylene glycol having an average molecular weight of about 8000.

4. The microencapsulated granule of claim 3 comprising about 15% by weight prednisone, about 15% by weight polyethylene glycol 800 and about 0.78% by weight hydroxypropyl methylcellulose.

5. The microencapsulated granule of claim 3 wherein the active coating is applied to the seed as an active coating composition having a total solids content of about 40% and comprising about 40% to about 60% prednisone based on total solids content, about 1.0% to about 5.0% hydroxypropy methylcellulose based on total solids content, about 40% to about 60% polyethylene glycol 8000 based on total solids content, and a solvent.

6. The microencapsulated granule of claim 5 wherein said solvent is selected from the group consisting of acetone, water, ethanol, methanol, isopropanol, chloroform, methylene chloride, methyl ethyl ketone, ethyl acetate, carbon tetrachloride, benzene and combinations thereof.

7. The microencapsulated granule of claim 6 wherein said solvent is water.

8. The microencapsulated granule of claim 1 further comprising about 7% by weight to about 15% by weight of a cationic copolymer of dimethylaminoethyl methacrylate and neutral methacrylic acid esters as a taste-mask coating over the active coating.

9. The microencapsulated granule of claim 4 further comprising about 10% by weight of a cationic copolymer of dimethylaminoethyl methacrylate and neutral methacrylic acid esters as a taste-mask coating over the active coating.

10. The microencapsulated granule of claim 8 wherein said copolymer is applied as a taste-mask coating composition comprising about 8% by weight to about 16% by weight of the cationic copolymer dissolved in a solvent.

11. The microencapsulated granule of claim 10 wherein said solvent is selected from the group consisting of methyl alcohol, ethyl alcohol, a 60/40 mixture of ethyl alcohol and water, isopropyl alcohol, n-butyl alcohol, propylene glycol, ethylene glycol, monobutyl ether, acetone, methyl ethyl ketone, cyclohexanone, methylene chloride, chloroform, carbon tetrachloride, trichloro ethylene, tetrachloro ethylene, ethylacetate, n-butyl acetate, toluene, propylene glycol acetate or any combination thereof in which the cationic copolymer is soluble.

12. The microencapsulated granule of claim 11 wherein said solvent comprises a mixture of about 40% by weight to about 60% by weight acetone and about 40% by weight to about 60% by weight isopropyl alcohol.

13. The microencapsulated granule of claim 8 further comprising a sufficient amount of an antistatic agent to uniformly cover the surface of the granule, said antistatic agent selected from the group consisting of silicon dioxide, talc, magnesium stearate, calcium stearate, polacrilin, stearic acid and combinations thereof.

14. The microencapsulated granule of claim 13 wherein said sufficient amount of an antistatic agent is from about 0.25% by weight to about 1.50% by weight of said granule.

15. The microencapsulated granule of claim 14 wherein said antistatic agent comprises about 0.75% by weight silicon dioxide.

16. The microencapsulated granule of claim 1 further comprising from about 10% to about 20% by weight of a plasticized mixture of about 60% by weight to about 90% by weight of ethylcellulose and about 10% by weight to about 40% by weight acetylated monoglycerides applied from an aqueous dispersion as a taste-mask coating over the active coating.

17. The microencapsulated granule of claim 16 wherein said plasticized mixture is applied as a taste-mask coating composition comprising about 10% by weight to about 40% by weight total solids in water.

18. The microencapsulated granule of claim 16 further comprising a sufficient amount of an antistatic agent to uniformly cover the surface of the granule, said antistatic agent selected from the group consisting of silicon dioxide, talc, magnesium stearate, calcium stearate, polocrilin, stearic acid and combinations thereof.

19. The microencapsulated granule of claim 18 wherein said sufficient amount of an antistatic agent is from about 0.25% by weight to about 1.50% by weight of said granule.

20. The microencapsulated granule of claim 19 wherein said antistatic agent comprises about 0.75% by weight silicon dioxide.

21. A process for manufacturing a prednisone microencapsulated granule comprising applying an active coating composition to an inert seed to form an active seed, said active coating composition having about 40% total solids content and comprising about 40% to about 60% prednisone based on total solids content, about 1.0% to about 5.0% binder based on total solids content, about 40% to about 60% dissolution promoter based on total solids content, and a solvent.

22. The process of claim 21 wherein said binder is selected from the group consisting of hydroxypropyl methylcellulose, polyvinylpyrrolidone, polyethylene oxide, hydroxypropyl cellulose and combinations thereof, and said dissolution promoter is selected from the group consisting of polyethylene glycol, sucrose, lactose and combinations thereof.

23. The process of claim 22 wherein said binder is hydroxypropyl methycellulose and said dissolution promoter is polyethylene glycol having an average molecular weight of about 8000.

24. The process of claim 21 wherein said solvent is selected from the group consisting of acetone, water, ethanol, methanol, isopropanol, chloroform, methylene chloride, methyl ethyl ketone, ethyl acetate, carbon tetrachloride, benzene and combinations thereof.

25. The process of claim 22 wherein said solvent is water.

26. The process of claim 23 further comprising the step of applying a taste-mask coating composition to the active seed, said taste-mask coating composition comprising about 8% by weight to about 16% by weight of a cationic copolymer of dimethylaminoethyl methacrylate and neutral methacrylic acid esters dissolved in a solvent.

27. The process of claim 26 wherein said solvent is selected from the group consisting of methyl alcohol, ethyl alcohol, a 60/40 mixture of ethyl alcohol and water, isopropyl alcohol, n-butyl alcohol, propylene glycol, ethylene glycol, monobutyl ether, acetone, methyl ethyl ketone, cyclohexanone, methylene chloride, chloroform, carbon tetrachloride, trichloro ethylene, tetrachloro ethylene, ethylacetate, n-butyl acetate, toluene, propylene glycol acetate or any combination thereof in which the cationic copolymer is soluble.

28. The process of claim 27 wherein said solvent comprises a mixture of about 40% by weight to about 60% by weight acetone and about 40% by weight to about 60% by weight isopropyl alcohol.

29. The process of claim 26 further comprising the step of applying a sufficient amount of an antistatic agent to uniformly cover the surface of the granule, said antistatic agent selected from the group consisting of silicon dioxide, talc, magnesium stearate, calcium stearate, polacrilin, stearic acid and combinations thereof.

30. The microencapsulated granule of claim 29 wherein said sufficient amount of an antistatic agent is from about 0.25% by weight to about 1.50% by weight of said granule.

31. The process of claim 30 wherein said antistatic agent comprises about 0.75% by weight silicon dioxide.

32. The process of claim 29 wherein the active coating composition, the taste-mask coating composition and the antistatic agent are applied by use of a fluidized bed technique.

33. The process of claim 23 further comprising the step of applying a taste-mask coating composition to the active seed, said taste-mask coating composition comprising a plasticized aqueous dispersion of about 10% by weight to about 30% by weight of ethylcellulose, about 3% by weight to about 30% by weight acetylated monoglycerides, and 50% by weight to 75% by weight water.

34. The process of claim 33 further comprising the step of applying a sufficient amount of an antistatic agent to uniformly cover the surface of the granule, said antistatic agent selected from the group consisting of silicon dioxide, talc, magnesium stearate, calcium stearate, polocrilin, stearic acid and combinations thereof.

35. The microencapsulated granule of claim 34 wherein said sufficient amount of an antistatic agent is from about 0.25% by weight to about 1.50% by weight of said granule.

36. The process of claim 35 wherein said antistatic agent comprises about 0.75% by weight silicon dioxide.

37. The process of claim 34 wherein the active coating composition, the taste-mask coating composition and the antistatic agent are applied by use of a fluidized bed technique.

38. A dosage delivery system comprising a plurality of prednisone microencapsulated granules as described in claim 1 compressed into a tablet.

39. A dosage delivery system comprising a plurality of prednisone microencapsulated granules as described in claim 1 contained in a water soluble capsule.

40. A dosage delivery system comprising a plurality of prednisone microencapsulated granules as described in claim 1 contained in a flowable material dispenser.

41. A dosage delivery system comprising a plurality of prednisone microencapsulated granules as described in claim 1 contained in unit dose packets, sachets, or blisters.

42. A dosage delivery system comprising a plurality of prednisone microencapsulated granules as described in claim 13 contained in a flowable material dispenser.

* * * * *